US00PP24731P2

(12) United States Plant Patent
Iredell et al.

(10) Patent No.: US PP24,731 P2
(45) Date of Patent: Aug. 5, 2014

(54) ***BOUGAINVILLEA* PLANT NAMED 'IREBABS3'**

(50) Latin Name: *Bougainvillea×spectro-glabra*
Varietal Denomination: IREBABS3

(71) Applicants: Janet Willa Iredell, Brisbane (AU); Peter Dawborn Iredell, Brisbane (AU)

(72) Inventors: Janet Willa Iredell, Brisbane (AU); Peter Dawborn Iredell, Brisbane (AU)

( * ) Notice: Subject to any disclaimer, the term of this patent is extended or adjusted under 35 U.S.C. 154(b) by 0 days.

(21) Appl. No.: 13/999,001

(22) Filed: Dec. 31, 2013

(51) Int. Cl.
*A01H 5/00* (2006.01)

(52) U.S. Cl.
USPC ..... Plt./256

(58) Field of Classification Search
USPC ..... Plt./256
See application file for complete search history.

*Primary Examiner* — Susan McCormick Ewoldt
(74) *Attorney, Agent, or Firm* — Barbara Campbell; Cochran Freund & Young LLC

(57) ABSTRACT

A *Bougainvillea* plant particularly distinguished by a rounded and spreading shrub and having purple bracts, is disclosed.

1 Drawing Sheet

Genus and species: *Bougainvillea×spectro-glabra.*
Variety denomination: 'IREBABS3'.

BACKGROUND OF THE NEW PLANT

The present invention comprises a new and distinct variety of *Bougainvillea*, botanically known as *Bougainvillea×spectro-glabra*, and hereinafter referred to by the variety name 'IREBABS3'. The new variety originated from an open-pollination with the female parent 'Pedro' (unpatented) and an unknown male *Bougainvillea* in October 1998 in Brisbane, Australia. A single plant selection was subsequently chosen in October 2000 in Brisbane, Australia for further evaluation and asexual propagation.

The new plant was first asexually propagated in October 2000 in Brisbane, Australia and has been asexually reproduced by cuttings for numerous generations in Brisbane, Australia. The present invention has been found to retain its distinctive characteristics through successive asexual propagations by cuttings.

'IREBABS3' has not been made publicly available or sold more than one year prior to the filing of this application.

SUMMARY

The following are the most outstanding and distinguishing characteristics of the new variety when grown under normal horticultural practices in Brisbane, Australia.

1. A rounded and spreading shrub; and
2. Having purple bracts.

DESCRIPTION OF THE PHOTOGRAPH

This new *Bougainvillea* plant is illustrated by the accompanying photograph which shows the foliage and bracts of the plant. The colors are as true as can be reasonably obtained by conventional photographic procedures. The photograph is of a plant less than one-year-old grown outdoors in Brisbane, Australia.

DESCRIPTION OF THE NEW VARIETY

The following detailed descriptions set forth the distinctive characteristics of 'IREBABS3'. The data which defines these characteristics were collected from asexual reproductions carried out in Brisbane, Australia. The plant history was taken in May 2013 on five-year-old plants grown outdoors in Brisbane, Australia. Color references were taken under natural light and are to The R.H.S. Colour Chart of The Royal Horticultural Society of London (R.H.S. 2005).

Classification:
- Family.—Nyctaginaceae.
- *Botanical name.—Bougainvillea×spectro-glabra.*
- *Common name.—Bougainvillea.*
- *Denomination.*—'IREBABS3'.

Plant:
- *Type.*—Shrub and perennial (in warmer climates).
- *Form.*—Rounded.
- *Habit.*—Low growing and spreading.
- *Appropriate containers.*—Commercial pots of all sizes.
- *Time to produce a finished flowering plant.*—12 weeks from a cutting.
- *Growth rate.*—Moderate.
- *Vigor.*—Strong.
- *Height (measured from the top of the soil).*—60.0 cm.
- *Width (horizontal plant diameter).*—Up to 100.0 cm.
- *Pinching required.*—Yes, at liner stage.
- *Propagation type.*—Cuttings.

Lateral branches:
- *Branching habit.*—Horizontal.
- *Length.*—60.0 cm.
- *Diameter.*—0.14 cm to 0.18 cm.
- *Internode length.*—1.4 cm to 1.6 cm.
- *Aspect.*—Horizontal.
- *Strength.*—Strong.
- *Color.*—RHS 199B.
- *Pubescence.*—Slightly puberulent.
- *Thorns.*—Size: 0.4 cm to 0.5 cm in length. Quantity: About 5% of the leaf nodes have thorns. Color: RHS 164C.

Foliage:
- *Arrangement.*—Alternate, single.
- *Appearance.*—Thick, dull.
- *Durability of foliage to stresses.*—Strong.
- *Quantity of leaves per lateral branch.*—Over 70.

*Shape*.—Broadly ovate.

*Apex*.—Acute.

*Base*.—Acute.

*Margin*.—Entire.

*Length*.—3.0 cm to 3.5 cm.

*Diameter*.—2.3 cm to 2.9 cm.

*Color, immature*.—Upper surface: RHS 139A. Lower surface: RHS 138A.

*Color, mature*.—Upper surface: RHS 137A. Lower surface: RHS 138A.

*Texture*.—Both upper and lower surfaces: Smooth.

*Venation type*.—Pinnate.

*Venation color*.—Upper surface: RHS 138A. Lower surface: RHS 138A.

*Petiole*.—Length: 0.4 cm to 0.5 cm. Diameter: 0.8 mm to 1.0 mm. Color: RHS 138A.

Inflorescence:

*General*.—Flowers all along the branch branchlets with flowers at each node.

*Height*.—About 4.0 cm.

*Width*.—About 5.0 cm.

*Bud*.—Shape: Urn-shaped. Length: 0.9 cm to 1.5 cm. Diameter: 0.5 cm to 1.2 cm. Color: Purple-violet.

*Flower*.—Type and habit: Single flowers arranged in axillary panicles; flowers are upright and self-cleaning. Fragrance: Absent. Aspect: Upright. Flowering season: Profuse flowering; flowers in autumn, the spring and regions with mild winters. Diameter: 3.2 cm to 3.5 cm. Depth: 3.0 cm. Quantity per lateral stem: Over 100. Quantity of flowers per inflorescence: 8 to 10. Flower tube (perianth): Color: RHS 155B. Diameter: 0.5 cm. Length: 2.5 cm. Quantity per flower: 3; composed of 5 fused petals. Bracts: Quantity per flower: 3. Length: 3.0 cm to 3.2 cm. Width: 2.1 cm to 2.3 cm. Shape: Broadly ovate. Apex: Acute. Base: Cordate. Margin: Entire. Texture (upper and lower surfaces): Velvety. Color, when opening: Upper surface: RHS N78C. Lower surface: RHS N78C. Color, when open: Upper surface: RHS N78A. Lower surface: RHS N78A. Peduncle: Length: 0.6 cm to 0.8 cm. Diameter: 0.1 cm. Angle: 30°. Strength: Strong. Color: RHS 138A. Pedicel: Length: 0.18 cm to 0.25 cm. Diameter: 0.1 mm. Angle: 25°. Strength: Moderate. Color: RHS 138A.

Fruit and seed set: None observed.

Disease and insect resistance: No specific disease or insect resistance observed.

Reproductive organs: None observed.

COMPARISON WITH PARENTAL AND COMMERCIAL VARIETY

'IREBABS3' differs from the female *Bougainvillea* parent 'Pedro' (unpatented), in that the 'IREBABS3' has purple bracts, while 'Pedro' has brick-red-orange bracts.

'IREBABS3' differs from the commercial comparison 'Koiro' (U.S. Plant Pat. No. 23,272) in that 'IREBABS3' has purple bracts, while 'Koiro' has red-purple bracts.

We claim:

1. A new and distinct variety of *Bougainvillea* plant as shown anal described herein.

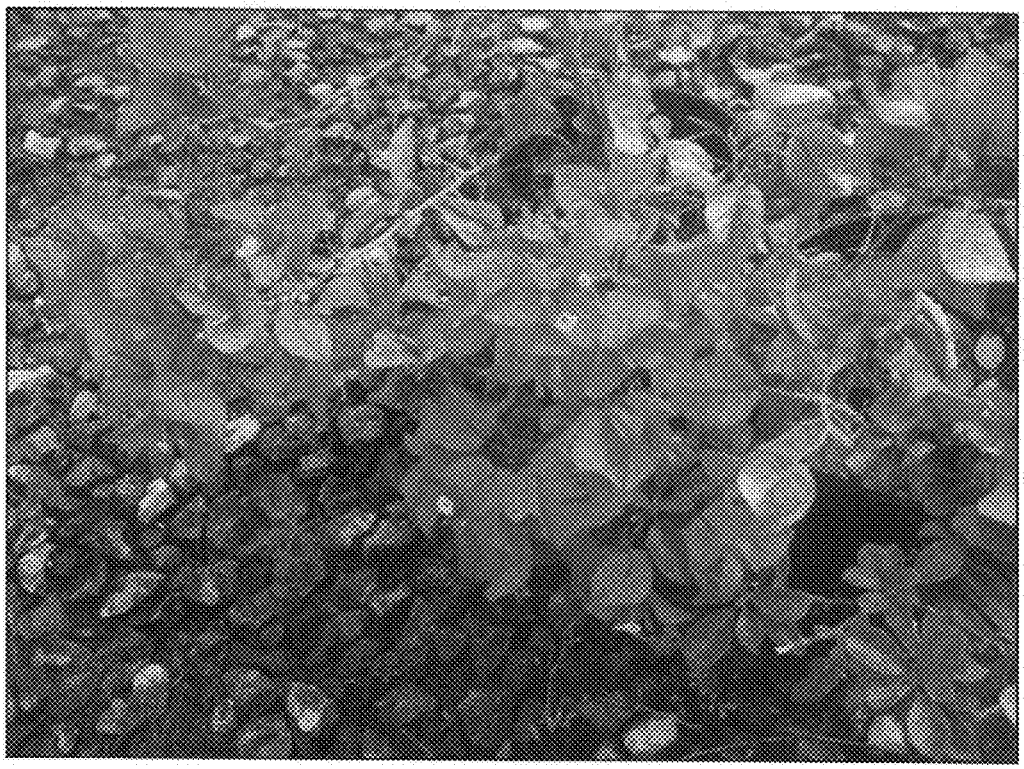

* * * * *